US011325972B2

(12) United States Patent
Hargreave et al.

(10) Patent No.: US 11,325,972 B2
(45) Date of Patent: *May 10, 2022

(54) METHODS OF TREATMENT OF EOSINOPHILIC BRONCHITIS WITH AN ANTI-IL-5 ANTIBODY (71) Applicant: GLAXOSMITHKLINE LLC, Wilmington, DE (US)

(72) Inventors: Fredrick E. Hargreave, Hamilton (CA); Giampietro Ventresca, Hertfordshire (GB)

(73) Assignee: GLAXOSMITHKLINE LLC, Wilmington, DE (US)

( * ) Notice: Subject to any disclaimer, the term of this patent is extended or adjusted under 35 U.S.C. 154(b) by 43 days.

This patent is subject to a terminal disclaimer.

(21) Appl. No.: 16/575,903

(22) Filed: Sep. 19, 2019

(65) Prior Publication Data
US 2020/0071395 A1   Mar. 5, 2020

Related U.S. Application Data (63) Continuation of application No. 15/804,104, filed on Nov. 6, 2017, now abandoned, which is a continuation of application No. 12/935,038, filed as application No. PCT/US2009/038509 on Mar. 27, 2009, now Pat. No. 9,834,600.

(60) Provisional application No. 61/040,363, filed on Mar. 28, 2008.

(51) Int. Cl.
*C07K 16/24* (2006.01)
*A61K 39/395* (2006.01)
*A61P 11/00* (2006.01)
*C07K 14/54* (2006.01)

(52) U.S. Cl.
CPC ........ *C07K 16/244* (2013.01); *A61K 39/3955* (2013.01); *A61P 11/00* (2018.01); *C07K 14/5409* (2013.01)

(58) Field of Classification Search
CPC .............. C07K 14/5409; C07K 16/244; A61K 39/3955; A61P 11/00
See application file for complete search history.

(56) References Cited

U.S. PATENT DOCUMENTS

| 4,980,359 A | 12/1990 | Hasspacher et al. |
| 5,096,704 A | 3/1992 | Coffman et al. |
| 5,455,337 A | 10/1995 | Devos et al. |
| 5,585,089 A | 12/1996 | Queen et al. |
| 5,683,892 A | 11/1997 | Ames et al. |
| 5,693,323 A | 12/1997 | Ames et al. |
| 5,783,184 A | 7/1998 | Applebaum et al. |
| 5,851,525 A | 12/1998 | Ames et al. |
| 6,129,913 A | 10/2000 | Ames et al. |
| 6,248,723 B1 | 6/2001 | Irvin |
| 6,555,566 B2 | 4/2003 | Ponikau |
| 6,946,130 B2 | 9/2005 | Ames et al. |
| 7,141,653 B2 | 11/2006 | Greenfeder et al. |
| 7,399,837 B2 | 7/2008 | Ames et al. |
| 7,422,742 B2 | 9/2008 | Greenfeder et al. |
| 9,834,600 B2 | 12/2017 | Hargreave et al. |
| 2003/0017169 A1 | 1/2003 | Pestka |
| 2003/0059429 A1 | 3/2003 | Ames et al. |
| 2003/0194404 A1 | 10/2003 | Greenfeder et al. |
| 2006/0029594 A1 | 2/2006 | Ames et al. |
| 2007/0025994 A1 | 2/2007 | Greenfeder et al. |
| 2009/0035216 A1 | 2/2009 | Svenson et al. |
| 2010/0086547 A1 | 4/2010 | Patel et al. |
| 2010/0158814 A1 | 6/2010 | Bussat et al. |

FOREIGN PATENT DOCUMENTS

| EP | 0 367 596 B1 | 12/1993 |
| EP | 0 800 536 | 12/1995 |
| JP | 06 141885 A | 5/1994 |
| WO | WO 1993/015210 | 8/1993 |
| WO | WO 1993/016184 | 8/1993 |
| WO | WO 1995/014040 | 5/1995 |
| WO | PCT/US1995/017082 | 12/1995 |
| WO | WO 1995/035375 | 12/1995 |
| WO | WO 1996/021000 | 7/1996 |
| WO | WO 1997/048418 | 12/1997 |
| WO | WO 2001/012646 | 2/2001 |
| WO | PCT/US2008/062019 | 4/2008 |
| WO | WO 2008/134721 A1 | 4/2008 |
| WO | WO 2008/134724 | 4/2008 |
| WO | WO 2012/109429 A3 | 2/2012 |

OTHER PUBLICATIONS

Menzies-Gow et al., "Anti-IL-5 (mepolizumab) therapy induces bone marrow eosinophil maturational arrest and decreases eosinophil progenitors in the bronchial mucosa of atopic asthmatics", Journal of Allergy Clinical Immunology, vol. 111, No. 4, pp. 714-719 (2003).
Singh et al.,"Anti-interleukin 5 strategies as a potential treatment for asthma", Thorax, vol. 52, pp. 483-485 (1997).
U.S. Appl. No. 60/914,833, filed Apr. 3, 2007, Bachert, et al..
U.S. Appl. No. 60/990,715, filed Nov. 28, 2007, Bachert, et al..
Letter by the Patentee dated Jul. 10, 2012 (EP 2 274 009 File History).
Garrett, et al., "Anti-interleukin-5 (mepolizumab) therapy for hypereosinophilic syndromes". Mechanisms of Allergy. J Allergy Clin Immunol, 113: 115-119 (online Dec. 12, 2013).
Klion, A., et al., Blood, 2004, 103(8), 2939-2941 "Brief Report: Safety and efficacy of the monoclonal anti-inteleukin-5 antibody SCH55700 in the treatment of patients with hypereosinophilic syndrome".

(Continued)

*Primary Examiner* — Zachary C Howard
(74) *Attorney, Agent, or Firm* — Cynthia Lan Martin; Duke Fitch (57) ABSTRACT

The present invention relates generally to the methods for the treatment and diagnosis of conditions mediated by IL-5 and excess eosinophil production, and more specifically to mAbs, Fabs, chimeric and humanized antibodies. More particularly, the present invention relates generally to the treatment of eosinophilic bronchitis with an anti-IL-5 antibody or fragment thereof.

24 Claims, 3 Drawing Sheets

Specification includes a Sequence Listing.

(56) References Cited

OTHER PUBLICATIONS

Kips, et al., "Effect of SCH55700, a humanized anti-human interleukin-5 antibody, in severe persistent Asthma: A pilot study". American Journal of Respiratory and Critical Care Medicine, 167, 1655-1659, (Mar. 30, 2003).
Drugs, R D, 9(2), 125-130 (Adis R&D Profile) "Mepolizumab—240563, Anti-IL-5 Monoclonal Antibody—GlaxoSmithKline—SB-240563" (Mar. 24, 2008).
"Phase III Study of Bosatria (mepolizumab) Showed Disease Control With Reduced Corticosteroid Use in Hypereosinophilic Syndrome"—Medical News Today (Press release) (Mar. 24, 2008).
Gibson, et al., Eosinophilic bronchitis: clinical manifestations and implications for treatment, Thorax, 2002, vol. 57, pp. 178-182, col. 2, paragraphs 1-3.
Hargreave, et al., 2004. Clin Exp Allergy, 34: 1807.
Busse, et al., 2010. J Allergy Clin Immunol. 125: 803-813.
Record for Registry No. 196078-29-2 (2011; Registry Database—ACS on STN; no author provided; 2 pages as printed).
Flood-Page et al. (2003. Am. J. Respir. Crit. Care, 167(2): 199-204).
Ames, et al., Journal of Immunology, Jun. 1995, 154(12): 6355-6364.
Bai, et al., A Guide to Dosing of Monoclonal Antibodies, Clin. Pharmacokinet., 51(2): 119-135, 2012.
Chee, et al., Pharma. Research, vol. 23, No. 6, pp. 1275-1284, 2006.
Collet, et al., PNAS USA, 89(21): 10026-10030 (Nov. 1, 1992).
Fokkens, et al., Rhinology, Supplement 20, Oct. 16, 2007 (Part 1 & Part 2).
Gevaert, et al., J. Allergy Clin. Immunol., 128(5): 989-995. E8, Nov. 2011.
Gnanakumaran, et al., Current Opinion in Molecular Therapeutics, Current Drugs, vol. 5, No. 3, pp. 321-325, Jun. 1, 2003.
Goldman, M., Bull Mem Acad R Med Belg. 2007; 162(1-2): 113-7; discussion 118-9.
Gunaratna, C., Current Separations, 19:3(2001), pp. 87-92.
Gurney, Howard, Journal Clinical Oncology, vol. 14, No. 9, Sep. 1996,: pp. 2590-2611.
Hart, Timothy K., et al. Journal of Allergy and Clinical Immunology, vol. 108, No. 2, pp. 250-257, Aug. 2001.
Hellmich, B., et al., Hypereosinophilic syndrome-recent developments in diagnosis and treatment. (Abstract). Dtsch Med WOchenschr, Sep. 2007; 132(37): 1892-6.
Kabat, et al., NIH PUBL, No. 91-3242, pp. 239 & 318; 1991.
Kettleborough, et al., Protein Engineering, Oct. 1991, 4(7): 773-783.
Lildholdt, T., et al. Clinical Otolaryagol., 20: 26-30, 1995.
Lund, et al., Arch. Otolaryngol. Head & Neck Surg., 124: 513-517, 1998.
Maggio, et al., Enzyme Immunoassay, pp. 167-178 (1980).
Mathijssen, et al., The Oncologist, 2007; 12: 913-923. www.TheOncologist.com.
McNamee, et al., Journal Immunol. Meth., 141, No. 1, pp. 81-88 (Aug. 1991).
Morrison, et al., PNAS, vol. 81, pp. 6851-6855, Nov. 1994.
Menard, et al., Annal Dell Instituto Superore Di Sanita, 27(1): 87-89 (1991).
Revill, P., et al., Drugs of the Future, vol. 32, No. 10, pp. 868-876, Oct. 2007.
Roufosse, F.E., et al., Hypereosinophilic syndromes (Abstract). Immunol. Allergy Clin. North Am., Aug. 2007; 27(3): 519-527.
Schwegman, J.J., et al., Pharmaceutical Development and Technology, vol. 10, pp. 151-173, 2005.
Teagarden, D.L., et al., European Journal of Pharmaceutical Sciences, vol. 15, pp. 115-133, 2002.
Tuncer, et al., Auris Nasus Larynx, 30(3):263-268, 2003.
U.S. Pat. No. 7,422,742 File history.
Vickova, et al., Rhinology, 47:419-426, 2009.
Wang, D., et al., Journal Clin. Pharmacol., 2009, 49:1012.
Zia-Amirhosseini, P., et al., Clinical Pharmacology and Therapeutics, vol. 65, No. 2, p. 147, Feb. 1, 1999.
Zia-Amirhosseini, P., et al., Journal of Pharmacology and Experimental Therapeutics, vol. 291, No. 3, pp. 1060-1067, Dec. 1999.
NCT00086658_2005_06_23.
NCT00086658_2005_06_30.
NCT00086658_2005_07_25.
NCT00086658_2005_08_01.
NCT00086658_2005_11_08.
NCT00086658_2005_12_08.
NCT00086658_2005_12_22.
NCT00086658_2006_04_18.
NCT00086658_2008_01_23.
NCT00097370_2005_06_23.
NCT00097370_2005_06_30.
NCT00097370_2005_07_25.
NCT00097370_2005_08_01.
NCT00097370_2005_12_08.
NCT00097370_2006_01_05.
NCT00097370_2006_09-27.
NCT00097370_2008_01_22.
NCT00097370_2008_03_19.
NCT00244686_2005_10_26.
NCT00244686_2005_11_09.
NCT00244686_2005_12_08.
NCT00244686_2006_05_30.
NCT00244686_2007_01_24.
NCT00244686_2007_01_26.
NCT00244686_2007_02_09.
NCT00244686_2007_02_11.
NCT00244686_2007_04_19.
NCT00244686_2007_05_15.
NCT00244686_2007_10_03.
NCT00244686_2008_02_20.
NCT00266565_2005_12_16.
NCT00266565_2005_12_19.
NCT00266565_2005_12_28.
NCT00266565_2006_05_26.
NCT00266565_2006_06_21.
NCT00266565_2006_06_27.
NCT00266565_2006_12_14.
NCT00266565_2007_01_23.
NCT00266565_2007_01_29.
NCT00266565_2007_02_05.
NCT00266565_2007_09_13.
NCT00266565_2008_04_03.
NCT00274703_2006_01_10.
NCT00274703_2006_09_27.
NCT00274703_2008_04_09.
NCT00292877_2006_02_15.
NCT00292877_2006_09_08.
NCT00292877_2007_03_06.
NCT00292877_2007_04_13.
NCT00358449_2006_07_28.
NCT00358449_2006_09_22.
NCT00358449_2006_12_21.
NCT00358449_2007_02_06.
NCT00358449_2007_03_18.
NCT00358449_2007_03_28.
NCT00358449_2007_04_19.
NCT00358449_2007_05_01.
NCT00358449_2007_08_17.
NCT00358449_2007_11_09.
NCT00358449_2008_02_28.
NCT00527566_2007_09_10.
NCT00527566_2008_05_11.
NCT00527566_2009_02_03.
NCT00527566_2009_04_18.
Global Initiative for Asthma 2007; pp. 1-92.
Jayaram, et al., Eur. Respir. J. 2006; 27: 483-494.
Korn, et al., Am. J. Crit. Care Med., 2007, 175, Abstract A486.
Nelson, et al., J. Allergy Clin. Immunol., 1999; 103: 267-275.

(56) References Cited

OTHER PUBLICATIONS

Pizzichini, M., et al., Am. J. Respir. Crit. Care Med., 1997; 155: 1501-1508.
Spahn, et al., J. Allergy Clin. Immunol., 1999; 103: 421-426.
Ten-Brinke, et al., Am. J. Respir. Crit. Care Med., 2004; 170: 601-605.
Paul O'Byrne, Am. J. Respir. Crit. Care Med., 2007; 176: 1059-1061.
Pizzichini, et al., Am. J. Respir. Crit. Care Med, 1998; 158: 1511-1517.
Pizzichini, et al., Eur. Respir. J. 1999; 13:15-21.
Lex, et al., Pediatric Pulmonology, 2007; 42:298-303.
Van Oosterhout Antoon J.M., et al., Effect of anti-IL-5 and IL-5 on airway hyperactivity and eosinophils in guinea pigs. vol. 147, No. 3, Jan. 1, 1993, pp. 548-552.
Chand, N., et al., Anti-IL-5 monoclonal antibody inhibits allergic late phase bronchial eosinophilia in guinea pigs., E. J. of Pharmacol., vol. 211, No. 1, Jan. 28, 1992, p. 121-23.
Rothenberg, et al., Treatment of Patients with Hypereosinophilic Syndrome with Mepolizumab., N.E.J. Med., Mar. 20, 2008, pp. 1215-1228.
Green, R.H., et al., Asthma exacerbations and sputum eosinophil counts: a randomised controlled trial., Lancet, vol. 360, No. 9347, Nov. 30, 2002, pp. 1715-1721.
Wechsler, Michael. Combating the Eosinophil with Anti-Interleukin-5 Therapy., N.E.J. Med., vol. 358, No. 12, Mar. 20, 2008, pp. 1293-1294.
Clinical Trials Gov. record for NCT00292887, Feb. 15, 2006 to Jan. 21, 2011.
Supplement to: Nair P, Pizzichini MMM, Kjarsgaard, M., et al., Mepolizumab for prednisone-dependent asthma with sputum eosinophilia. N Engl. J. Med., 2009, 360:985-93.
Sanderson, CJ. The Biological role of interleukin 5. Int. J. Cell. Cloning, 1990, 8:147-53.
Borish, et al., Updates and cytokines. J. of Allergy and Clin. Immunol., vol. 97, No. 3, Mar. 1, 1996, pp. 719-733.
Djukanovic, R., et al. Am. Rev. Respir. Dis., 1990; 142: 434-457.
Djukanovic, R., et al. Eur. Respir. J., 2002, 20: Suppl 37, 1s-55s.
Pavord, ID, Brightling CE. Lancet, Jun. 26, 1999; 353(9171): 2213-4.
Nair, P., et al., Am. J. Respir. Crit. Care Med., Apr. 2008; 177.
P. Flood-Page et al., A Study to Evaluate Safety and Efficacy of Mepo in Patients with Asthma. Am. J. Resp. Crit. Care Med., 176, No. 11, Jan. 1, 2007, pp. 1062-1071.
Haldar, et al., Mepolizumab and Exacerbations of Refractory Eosinophilic Asthma. The New England Journal of Medicine, vol. 360, No. 10, Mar. 5, 2009, pp. 973-984.
Leckie, et al. Effects of an interleukin-5 blocking monoclonal antibody on eosinophils, airway hyper-responsiveness, and the late asthmatic response. The Lancet, vol. 356, Dec. 23, 2000, pp. 2144-2148.
Nair, et al. Mepolizumab for Prednisone-Dependent Asthma with Sputum Eosinophilia. The New England Journal of Medicine, vol. 360, No. 10, Mar. 5, 2009, pp. 985-993.
Smith, et al. Pharmacokinetics and Pharmacodynamics of Mepolizumab, an Anti-Interleukin-5 Monoclonal Antibody. Clin. Pharmacokinet., 2011, vol. 50(4): 215-227.

SEQUENCE LISTING

<160> NUMBER OF SEQ ID NOS: 21

<210> SEQ ID NO 1
<211> LENGTH: 334
<212> TYPE: DNA
<213> ORGANISM: Murine

<400> SEQUENCE: 1

| acctggcctg gtggcgccct cacagagcct gtccatcact tgcactgtct ctgggttttc | 60 |
| attaaccagc tatagtgtac actgggttcg ccagcctcca ggaaagggtc tggagtggct | 120 |
| gggagtaata tgggctagtg gaggcacaga ttataattcg gctctcatgt ccagactgag | 180 |
| catcagcaaa gacaactcca agagccaagt tttcttaaaa ctgaacagtc tgcaaactga | 240 |
| tgacacagcc atgtactact gtgccagaga tcccccttct tccttactac ggcttgacta | 300 |
| ctggggccaa ggcaccactc tcacagtctc ctca | 334 |

<210> SEQ ID NO 2
<211> LENGTH: 315
<212> TYPE: DNA
<213> ORGANISM: Murine

<400> SEQUENCE: 2

| tcctcccctga gtgtgtcagc aggagagaag gtcactatga gctgcaagtc cagtcagagt | 60 |
| ctgttaaaca gtggaaatca aaagaactac ttggcctggt accagcagaa accagggcag | 120 |
| cctcctaaac ttttgatcta cggggcatcc actagggaat ctggggtccc tgatcgcttc | 180 |
| acaggcagtg gatctggaac cgatttcact cttttccatca gcagtgtgca ggctgaagac | 240 |
| ctggcagttt attactgtca gaatgttcat agttttccat tcacgttcgg ctcggggaca | 300 |
| gagttggaaa taaaa | 315 |

<210> SEQ ID NO 3
<211> LENGTH: 334
<212> TYPE: DNA
<213> ORGANISM: Murine

<400> SEQUENCE: 3

| acctggcctg gtggcgccct cacagagcct gtccatcact tgcactgtct ctgggttttc | 60 |
| attaaccagt tatagtgtac actgggttcg ccagcctcca ggaaagggtc tggagtggct | 120 |
| gggagtaata tgggctagtg gaggcacaga ttataattcg gctctcatgt ccagactgag | 180 |
| catcagcaaa gacaactcca agagccaagt tttcttaaaa ctgaacagtc tgcgaactga | 240 |
| tgacacagcc atgtactact gtgccagaga tcccccttct tccttactac ggcttgacta | 300 |
| ctggggccaa ggcaccactc tcacagtctc ctca | 334 |

<210> SEQ ID NO 4
<211> LENGTH: 315
<212> TYPE: DNA
<213> ORGANISM: Murine

<400> SEQUENCE: 4

| tcctcccctga gtgtgtcagc aggagagaag gtcactatga gctgcaagtc cagtcagagt | 60 |
| ctattaaaca gtggaaatca aaagaactac ttggcctggt accaacagaa accagggcag | 120 |
| cctcctaaac ttttgatcta cggggcatcc actagggaat ctggggtccc tgatcgcttc | 180 |
| acaggcagtg gatctggaac cgatttcact cttaccatca gcagtgtgca ggctgaagac | 240 |

-continued

```
ctggcagttt attactgtca gaatgatcat agttttccat tcacgttcgg ctcggggaca      300
gagttggaaa taaaa                                                        315

<210> SEQ ID NO 5
<211> LENGTH: 334
<212> TYPE: DNA
<213> ORGANISM: Murine

<400> SEQUENCE: 5
acctggcctg gtggcgccct cacagagcct gtccatcact tgcactgtct ctgggttttc       60
attaaccagc tatagtgtac actgggttcg ccagcctcca ggaaagggtc tggagtggct      120
gggagtaatc tgggctagtg gaggcacaga ttataattcg gctctcatgt ccagactgag      180
catcagcaaa gacaactcca agagccaagt tttcttaaaa ctgaacagtc tgcaaactga      240
tgacgcagcc atgtactact gtgccagaga tccccctttt tccttactac ggcttgactt      300
ctggggccaa ggcaccactc tcacagtctc ctca                                  334

<210> SEQ ID NO 6
<211> LENGTH: 315
<212> TYPE: DNA
<213> ORGANISM: Murine

<400> SEQUENCE: 6
tcctctctga gtgtgtcagc aggagagaag gtcactatga gctgcaagtc cagtcagagt       60
ctgttaaaca gtggaaatca aaaaaactac ttggcctggt accagcagaa accagggcag      120
cctcctaaac ttttgatcta cggggcatcc actaggggaat ctggggtccc tgatcgcttc      180
acaggcagtg gatctggaac cgatttcact cttaccatca gcagtgtgca ggctgaagac      240
ctggcagttt attactgtca gaatgatcat agttttccat tcacgttcgg ctcggggaca      300
gagttggaaa taaaa                                                        315

<210> SEQ ID NO 7
<211> LENGTH: 5
<212> TYPE: PRT
<213> ORGANISM: Murine

<400> SEQUENCE: 7

Ser Tyr Ser Val His
1               5

<210> SEQ ID NO 8
<211> LENGTH: 16
<212> TYPE: PRT
<213> ORGANISM: Murine

<400> SEQUENCE: 8

Val Ile Trp Ala Ser Gly Gly Thr Asp Tyr Asn Ser Ala Leu Met Ser
1               5                   10                  15

<210> SEQ ID NO 9
<211> LENGTH: 11
<212> TYPE: PRT
<213> ORGANISM: Murine

<400> SEQUENCE: 9

Asp Pro Pro Ser Ser Leu Leu Arg Leu Asp Tyr
1               5                   10
```

```
<210> SEQ ID NO 10
<211> LENGTH: 17
<212> TYPE: PRT
<213> ORGANISM: Murine

<400> SEQUENCE: 10

Lys Ser Ser Gln Ser Leu Leu Asn Ser Gly Asn Gln Lys Asn Tyr Leu
1               5                   10                  15

Ala

<210> SEQ ID NO 11
<211> LENGTH: 7
<212> TYPE: PRT
<213> ORGANISM: Murine

<400> SEQUENCE: 11

Gly Ala Ser Thr Arg Glu Ser
1               5

<210> SEQ ID NO 12
<211> LENGTH: 9
<212> TYPE: PRT
<213> ORGANISM: Murine

<400> SEQUENCE: 12

Gln Asn Val His Ser Phe Pro Phe Thr
1               5

<210> SEQ ID NO 13
<211> LENGTH: 9
<212> TYPE: PRT
<213> ORGANISM: Murine

<400> SEQUENCE: 13

Gln Asn Asp His Ser Phe Pro Phe Thr
1               5

<210> SEQ ID NO 14
<211> LENGTH: 11
<212> TYPE: PRT
<213> ORGANISM: Murine

<400> SEQUENCE: 14

Asp Pro Pro Phe Ser Leu Leu Arg Leu Asp Phe
1               5                   10

<210> SEQ ID NO 15
<211> LENGTH: 119
<212> TYPE: PRT
<213> ORGANISM: Artificial Sequence
<220> FEATURE:
<223> OTHER INFORMATION: Murine/Homo sapiens

<400> SEQUENCE: 15

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Ser Val His Trp Val Arg Gln Pro Pro Gly Lys Gly Leu Glu Trp Leu
        35                  40                  45

Gly Val Ile Trp Ala Ser Gly Gly Thr Asp Tyr Asn Ser Ala Leu Met
    50                  55                  60
```

```
Ser Arg Leu Ser Ile Ser Lys Asp Asn Ser Lys Ser Gln Val Phe Leu
 65                  70                  75                  80

Lys Leu Asn Ser Leu Gln Thr Asp Asp Thr Ala Met Tyr Tyr Cys Ala
                 85                  90                  95

Arg Asp Pro Pro Ser Ser Leu Leu Arg Leu Asp Tyr Trp Gly Gln Gly
            100                 105                 110

Thr Thr Leu Thr Val Ser Ser
        115

<210> SEQ ID NO 16
<211> LENGTH: 113
<212> TYPE: PRT
<213> ORGANISM: Artificial Sequence
<220> FEATURE:
<223> OTHER INFORMATION: Murine/Homo sapiens

<400> SEQUENCE: 16

Asp Ile Val Met Thr Gln Ser Pro Ser Ser Leu Ser Val Ser Ala Gly
 1               5                  10                  15

Glu Lys Val Thr Met Ser Cys Lys Ser Ser Gln Ser Leu Leu Asn Ser
             20                  25                  30

Gly Asn Gln Lys Asn Tyr Leu Ala Trp Tyr Gln Gln Lys Pro Gly Gln
         35                  40                  45

Pro Pro Lys Leu Leu Ile Tyr Gly Ala Ser Thr Arg Glu Ser Gly Val
     50                  55                  60

Pro Asp Arg Phe Thr Gly Ser Gly Ser Gly Thr Asp Phe Thr Leu Ser
 65                  70                  75                  80

Ile Ser Ser Val Gln Ala Glu Asp Leu Ala Val Tyr Tyr Cys Gln Asn
                 85                  90                  95

Val His Ser Phe Pro Phe Thr Phe Gly Ser Gly Thr Glu Leu Glu Ile
            100                 105                 110

Lys

<210> SEQ ID NO 17
<211> LENGTH: 60
<212> TYPE: DNA
<213> ORGANISM: Homo sapiens

<400> SEQUENCE: 17
atggtgttgc agacccaggt cttcatttct ctgttgctct ggatctctgg tgcctacggg    60

<210> SEQ ID NO 18
<211> LENGTH: 357
<212> TYPE: DNA
<213> ORGANISM: Artificial Sequence
<220> FEATURE:
<223> OTHER INFORMATION: Murine/Homo sapiens - humanized

<400> SEQUENCE: 18
caggttaccc tgcgtgaatc cggtccggca ctagttaaac cgacccagac cctgacgtta    60
acctgcaccg tctccggttt ctcccctgacg agctatagtg tacactgggt ccgtcagccg   120
ccgggtaaag gtctagaatg gctgggtgta atatgggcta gtggaggcac agattataat   180
tcggctctca tgtcccgtct gtcgatatcc aaagacacct cccgtaacca ggttgttctg   240
accatgacta catggaccc gggttgacac cgctaccact actgcgctcg agatcccct     300 tcttccttac tacggcttga ctactgggt cgtggtaccc cagttaccgt gagctca        357
```

<210> SEQ ID NO 19
<211> LENGTH: 119
<212> TYPE: PRT
<213> ORGANISM: Artificial Sequence
<220> FEATURE:
<223> OTHER INFORMATION: Murine/Homo sapiens - humanized

<400> SEQUENCE: 19

```
Gln Val Thr Leu Arg Glu Ser Gly Pro Ala Leu Val Lys Pro Thr Gln
1               5                   10                  15

Thr Leu Thr Leu Thr Cys Thr Val Ser Gly Phe Ser Leu Thr Ser Tyr
            20                  25                  30

Ser Val His Trp Val Arg Gln Pro Pro Gly Lys Gly Leu Glu Trp Leu
        35                  40                  45

Gly Val Ile Trp Ala Ser Gly Gly Thr Asp Tyr Asn Ser Ala Leu Met
    50                  55                  60

Ser Arg Leu Ser Ile Ser Lys Asp Thr Ser Arg Asn Gln Val Val Leu
65                  70                  75                  80

Thr Met Thr Asn Met Asp Pro Val Asp Thr Ala Thr Tyr Tyr Cys Ala
                85                  90                  95

Arg Asp Pro Pro Ser Ser Leu Leu Arg Leu Asp Tyr Trp Gly Arg Gly
            100                 105                 110

Thr Pro Val Thr Val Ser Ser
        115
```

<210> SEQ ID NO 20
<211> LENGTH: 339
<212> TYPE: DNA
<213> ORGANISM: Artificial Sequence
<220> FEATURE:
<223> OTHER INFORMATION: Murine/Homo sapiens - humanized

<400> SEQUENCE: 20

```
gatatcgtga tgacccagtc tccagactcg ctagctgtgt ctctgggcga gagggccacc      60
atcaactgca agagctctca gagtctgtta aacagtggaa atcaaaagaa ctacttggcc     120
tggtatcagc agaaacccgg gcagcctcct aagttgctca tttacggggc gtcgactagg     180
gaatctgggg tacctgaccg attcagtggc agcgggtctg ggacagattt cactctcacc     240
atcagcagcc tgcaggctga agatgtggca gtatactact gtcagaatgt tcatagtttt     300
ccattcacgt tcggcggagg gaccaagttg gagatcaaa                            339
```

<210> SEQ ID NO 21
<211> LENGTH: 113
<212> TYPE: PRT
<213> ORGANISM: Artificial Sequence
<220> FEATURE:
<223> OTHER INFORMATION: Murine/Homo sapiens - humanized

<400> SEQUENCE: 21

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Gly Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80
```

-continued

```
Ile Ser Ser Leu Gln Ala Glu Asp Val Ala Val Tyr Tyr Cys Gln Asn
                85                  90                  95

Val His Ser Phe Pro Thr Phe Gly Gly Gly Thr Lys Leu Glu Ile
            100                 105                 110

Lys
```

METHODS OF TREATMENT OF EOSINOPHILIC BRONCHITIS WITH AN ANTI-IL-5 ANTIBODY

This application is a Continuation of U.S. application Ser. No. 15/804,104, filed 6 Nov. 2017, which is a Continuation of U.S. application Ser. No. 12/935,038, filed 28 Sep. 2010, which is a § 371 of International Application No. PCT/US2009/038509, filed 27 Mar. 2009, which claims the benefit of US Provisional Application No. 61/040,363 filed 28 Mar. 2008 which is incorporated herein in their entireties.

FIELD OF THE INVENTION

The present invention relates generally to the methods for the treatment and diagnosis of conditions mediated by IL-5 and excess eosinophil production, and more specifically to the treatment of eosinophilic bronchitis with an anti-IL-5 antibody.

BACKGROUND OF THE INVENTION

Eosinophils have been implicated in the pathogenesis of a wide variety of inflammatory disease states including allergic disorders associated with hypersensitivity reactions in the lung tissue (Butterfield et al., In: *Immunopharmacology of Eosinophils*, H. Smith and R. Cook, Eds., p. 151-192, Academic Press, London (1993)). A notable example is asthma, a disease characterized by reversible obstruction of the airways leading to non-specific bronchial hyperresponsiveness. This in turn is dependent upon the generation of a chronic inflammatory reaction at the level of the bronchial mucosa and a characteristic infiltration by macrophages, lymphocytes and eosinophils. The eosinophil appears to play a central role in initiating the mucosal damage typical of the disease (Corrigan et al., *Immunol. Today*, 13:501-507 (1992)). Increased numbers of activated eosinophils have been reported in the circulation, bronchial secretions and lung parenchyma of patients with chronic asthma, and the severity of the disease, as measured by a variety of lung function tests, correlates with blood eosinophil numbers (Griffen et al., *J. Aller. Clin. Immunol.*, 67:548-557 (1991)). Increased numbers of eosinophils, often in the process of degranulation, have also been recovered in bronchoalveolar lavage (BAL) fluids of patients undergoing late asthmatic reactions, and reducing eosinophil numbers, usually as a consequence of steroid therapy, is associated with improvements in clinical symptoms (Bousquet et al., *N. Eng. J. Med.*, 323:1033-1039 (1990)).

Interleukin 5 (IL-5) is a homodimeric glycoprotein produced predominantly by activated CD4+ T lymphocytes. In man, IL-5 is largely responsible for controlling the growth and differentiation of eosinophils. Elevated levels of IL-5 are detected in the bronchoalveolar lavage washings of asthmatics (Motojima et al., *Allergy*, 48:98 (1993)). Mice which are transgenic for IL-5 show a marked eosinophilia in peripheral blood and tissues in the absence of antigenic stimulation (Dent et al., *J. Exp. Med.*, 172:1425 (1990)) and anti-murine IL-5 monoclonal antibodies have been shown to have an effect in reducing eosinophilia in the blood and tissues of mice (Hitoshi et al., *Int. Immunol.*, 3:135 (1991)) as well as the eosinophilia associated with parasite infection and allergen challenge in experimental animals (Coffman et al., *Science*, 245:308-310 (1989), Sher et al., *Proc. Natl. Acad. Sci.*, 83:61-65 (1990), Chand et al., *Eur. J. Pharmacol.*, 211:121-123 (1992)).

Eosinophilic airway inflammation, an eosinophilic bronchitis, is the component of asthma known to predict response to treatment with corticosteroids (Hargreave, F E, J *Allergy Clin Immunol*, 102:S102-5 (1998)). It is identified by sputum eosinophilia and can also occur in patients without asthma (Hargreave, F E and Paramerwaran, K. *Eur Respir J*, 28:264-7 (2006)). In patients with asthma (Jayaram, et al. *Eur Respir J.* 27:483-94 (2006)) or chronic obstructive pulmonary disease (Siva, et al. *Eur Respir J*, 29:906-13 (2007)), normalizing airway eosinophils improves asthma control and prevents exacerbation.

Although corticosteroids are extremely effective in suppressing eosinophil numbers and other inflammatory components of asthma and eosinophilic bronchitis, there are concerns about their side effects in both severe asthmatics and more recently in mild to moderate asthmatics. The only other major anti-inflammatory drug therapies—cromoglycates (cromolyn sodium and nedocromil)—are considerably less effective than corticosteroids and their precise mechanism of action remains unknown.

At present, there is no outstanding drug which can have a prednisone-sparing effect in the treatment of eosinophilic bronchitis. Thus, there is a need for the methods of the present invention to reduce eosinophils in a human in need thereof.

SUMMARY OF THE INVENTION

In one embodiment of the present invention, methods are provided for treating eosinophilic bronchitis, comprising administering to said human suffering from eosinophilic bronchitis a composition comprising at least one anti-IL-5 antibody.

BRIEF DESCRIPTION OF THE DRAWINGS

FIG. 3: Eosinophils in Sputum (Panel A) and Blood (Panel B). Shown are the mean proportions of eosinophils in sputum and numbers of eosinophils in blood study entry (V1), 4 weeks after the first infusion of a study drug (V4), and at the completion of study treatment (V12) in the two study groups. In the mepolizumab group, one patient was withdrawn because of an adverse event. One patient in the mepolizumab group and nine in the placebo group had an exacerbation before the study was complete. V4 sputum was not obtained from one patient. One patient in the mepolizumab group and one patient in the placebo group were enrolled in the study in error, since they did not have sputum eosinophilia at baseline. The dashed lines indicate normal values.

DETAILED DESCRIPTION OF THE INVENTION

I. Definitions.

As used herein an "anti-IL-5 antibody" refers to any antibody, antibody fragment or single chain antibody that binds to IL-5 from any species. Antibody fragments include antibodies lacking all or part of an immunoglobulin constant region, e.g., Fv, Fab, or F(ab)$_2$ and the like. An anti-IL-5 antibody may be murine, chimeric, humanized or fully human. The antibody may be neutralizing. Several examples of anti-IL-5 antibodies are described in U.S. Pat. Nos.

5,683,892, 5,693,323, 5,783,184, 5,851,525, 6,129,913, 5,096,071, 6,056,957, and 6,451,982 herein incorporated by reference in their entirety. In addition, humanized anti-IL-5 antibodies are described in various references and include relizumab (SCH55700) and mepolizumab (SB240563) (Greenfeder, et al., *Respiratory Research*, 2(2):71-79 (2001)). Mepolizumab (SB-240563) is a fully humanized monoclonal antibody (IgG$_1$, kappa, mAb) which is specific for human interleukin-5 (IL-5). Other anti-IL-5 antibodies are described in U.S. Pat. Nos. 7,422,742 and 7,141,653 also incorporated herein by reference.

"Neutralizing" refers to an antibody that inhibits IL-5 activity by preventing the binding of human IL-5 to its specific receptor or by inhibiting the signalling of IL-5 through its receptor, should binding occur. A mAb is neutralizing if it is 90% effective, 95% effective or 100% effective in inhibiting IL-5 activity as measured in the B13 cell bioassay. Antibody binding can be measured by a number of assays known in the art including using a BIAcore optical biosensor (Pharmacia Biosensor, Uppsala, Sweden) and/or an ELISA assay.

The term "high affinity" refers to an antibody having a binding affinity characterized by a $K_d$ equal to or less than $3.5 \times 10^{-11}$ M for human IL-5 as determined by optical biosensor anaylsis. The $K_d$ for IL-5 of a Fab fragment might be estimated to be about $9 \times 10^{-11}$ M as determined by optical biosensor.

By "binding specificity for human IL-5" is meant that the antibody has a higher affinity for human IL-5 compared with any non-human IL-5 orthologue such as, but not limited to, murine IL-5. For instance, an antibody with binding specificity for human IL-5 might have a $K_d$ equal to or less than $2.2 \times 10^{-11}$M for human IL-5 while having a $K_d$ of greater than $2.2 \times 10^{-11}$M for non-human IL-5 orthologue.

The terms Fv, Fc, Fd, Fab, or F(ab)$_2$ are used with their standard meanings (see, e.g., Harlow et al., *Antibodies A Laboratory Manual*, Cold Spring Harbor Laboratory, (1988)).

As used herein, an "engineered antibody" describes a type of altered antibody, i.e., a full-length synthetic antibody (e.g., a chimeric or humanized antibody as opposed to an antibody fragment) in which a portion of the light and/or heavy chain variable domains of a selected acceptor antibody are replaced by analogous parts from one or more donor antibodies which have specificity for the selected epitope. For example, such molecules may include antibodies characterized by a humanized heavy chain associated with an unmodified light chain (or chimeric light chain), or vice versa. Engineered antibodies may also be characterized by alteration of the nucleic acid sequences encoding the acceptor antibody light and/or heavy variable domain framework regions in order to retain donor antibody binding specificity. These antibodies can comprise replacement of one or more CDRs (preferably all) from the acceptor antibody with CDRs from a donor antibody described herein.

A "chimeric antibody" refers to a type of engineered antibody which contains naturally-occurring variable region (light chain and heavy chains) derived from a donor antibody in association with light and heavy chain constant regions derived from an acceptor antibody.

A "humanized antibody" refers to a type of engineered antibody having its CDRs derived from a non-human donor immunoglobulin, the remaining immunoglobulin-derived parts of the molecule being derived from one (or more) human immunoglobulin(s). In addition, framework support residues may be altered to preserve binding affinity (see, e.g., Queen et al., *Proc. Natl Acad Sci USA*, 86:10029-10032 (1989), Hodgson et al., *Bio/Technology*, 9:421 (1991)).

The term "donor antibody" refers to an antibody (monoclonal or recombinant) which contributes the nucleic acid sequences of its variable regions, CDRs, or other functional fragments or analogs thereof to a first immunoglobulin partner, so as to provide the altered immunoglobulin coding region and resulting expressed altered antibody with the antigenic specificity and neutralizing activity characteristic of the donor antibody. One donor antibody suitable for use in this invention is a non-human neutralizing monoclonal antibody (i.e., murine) designated as 2B6 (see U.S. Pat. Nos. 5,683,892, 5,693,323, 5,783,184, 5,851,525, and 6,129,913 herein incorporated by reference in their entirety). The antibody 2B6 is defined as a high affinity, human-IL-5 specific (i.e., does not recognize murine IL-5), neutralizing antibody of isotype IgG$_1$ having the variable light chain DNA and amino acid sequences of SEQ ID NOs: 2 and 16, respectively, and the variable heavy chain DNA and amino acid sequences of SEQ ID NOs: 1 and 15, respectively, on a suitable murine IgG constant region.

The term "acceptor antibody" refers to an antibody (monoclonal or recombinant) heterologous to the donor antibody, which contributes all (or any portion, but preferably all) of the nucleic acid sequences encoding its heavy and/or light chain framework regions and/or its heavy and/or light chain constant regions to the first immunoglobulin partner. Preferably a human antibody is the acceptor antibody.

"CDRs" are defined as the complementarity determining region amino acid sequences of an antibody which are the hypervariable regions of immunoglobulin heavy and light chains. See, e.g., Kabat et al., *Sequences of Proteins of Immunological Interest*, 4th Ed., U.S. Department of Health and Human Services, National Institutes of Health (1987). There are three heavy chain and three light chain CDRs (or CDR regions) in the variable portion of an immunoglobulin. Thus, "CDRs" as used herein refers to all three heavy chain CDRs, or all three light chain CDRs (or both all heavy and all light chain CDRs, if appropriate).

CDRs provide the majority of contact residues for the binding of the antibody to the antigen or epitope. CDRs of interest in this invention are derived from donor antibody variable heavy and light chain sequences, and include analogs of the naturally occurring CDRs, which analogs also share or retain the same antigen binding specificity and/or neutralizing ability as the donor antibody from which they were derived.

By 'sharing the antigen binding specificity or neutralizing ability' is meant, for example, that although mAb 2B6 (see U.S. Pat. Nos. 5,683,892, 5,693,323, 5,783,184, 5,851,525, and 6,129,913 herein incorporated y reference) may be characterized by a certain level of antigen affinity, a CDR encoded by a nucleic acid sequence of 2B6 in an appropriate structural environment may have a lower, or higher affinity. It is expected that CDRs of 2B6 in such environments will nevertheless recognize the same epitope(s) as 2B6. Exemplary heavy chain CDRs of 2B6 include SEQ ID NO: 7; SEQ ID NO: 8; SEQ ID NO: 9; and exemplary light chain CDRs of 2B6 include SEQ ID NO: 10; SEQ ID NO: 11; and SEQ ID NO: 12.

A "functional fragment" is a partial heavy or light chain variable sequence (e.g., minor deletions at the amino or carboxy terminus of the immunoglobulin variable region) which retains the same antigen binding specificity and/or neutralizing ability as the antibody from which the fragment was derived.

An "analog" is an amino acid sequence modified by at least one amino acid, wherein said modification can be chemical or a substitution or a rearrangement of a few amino acids (i.e., no more than 10), which modification permits the amino acid sequence to retain the biological characteristics, e.g., antigen specificity and high affinity, of the unmodified sequence. For example, (silent) mutations can be constructed, via substitutions, when certain endonuclease restriction sites are created within or surrounding CDR-encoding regions.

Analogs may also arise as allelic variations. An "allelic variation or modification" is an alteration in the nucleic acid sequence encoding the amino acid or peptide sequences of the invention. Such variations or modifications may be due to degeneracy in the genetic code or may be deliberately engineered to provide desired characteristics. These variations or modifications may or may not result in alterations in any encoded amino acid sequence.

The term "effector agents" refers to non-protein carrier molecules to which the altered antibodies, and/or natural or synthetic light or heavy chains of the donor antibody or other fragments of the donor antibody may be associated by conventional means. Such non-protein carriers can include conventional carriers used in the diagnostic field, e.g., polystyrene or other plastic beads, polysaccharides, e.g., as used in the BIAcore [Pharmacia] system, or other non-protein substances useful in the medical field and safe for administration to humans and animals. Other effector agents may include a macrocycle, for chelating a heavy metal atom, or radioisotopes. Such effector agents may also be useful to increase the half-life of the altered antibodies, e.g., polyethylene glycol.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as posttranslational processing, or by chemical modification techniques that are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, PROTEINS—STRUCTURE AND MOLECULAR PROPERTIES, 2nd Ed., T. E. Creighton, W. H. Freeman and Company, New York, 1993 and Wold, F., Posttranslational Protein Modifications: Perspectives and Prospects, pgs. 1-12 in POSTTRANSLATIONAL COVALENT MODIFICATION OF PROTEINS, B. C. Johnson, Ed., Academic Press, New York, 1983; Seifter, et al., "Analysis for protein modifications and nonprotein cofactors", *Meth. Enzymol.* (1990) 182:626-646 and Rattan, et al., "Protein Synthesis: Posttranslational Modifications and Aging", *Ann NY Acad Sci* (1992) 663:48-62.

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

As used herein "eosinophilic bronchitis" refers to a condition in which a mammal has quantitative sputum cell counts (eosinophils greater than 2%) which is responsive to corticosteroid treatment. It may occur alone or in association with asthma or in some patients with chronic obstructive pulmonary disease (COPD). Typically, in comparison to asthmatic patients, those with eosinophilic bronchitis experience the symptom of cough alone and have both normal lung function and airway responsiveness (Thomson and Chaudhuri *American Journal of Respiratory and Critical Care Medicine* 170:4-5 (2004), and Gibson, et al. *Thorax* 57:178-182 (2002)). In most patients the eosinophilic bronchitis responds to treatment with inhaled steroids but in some it requires a minimum dose of prednisone to keep it controlled. Eosinophilic bronchitis and/or asthma can be considered severe in a patient when the patient requires at least 35-40 mg/day of predisone to control the symptoms of either condition.

As used herein "airway eosinophilia" refers to any disease or disorder in which a patient has any amount of eosinophils in any airway, including but not limited to, lung. Eosinophils may be detected, for example, in or by biopsy, sputum, and/or lavage. Diseases associated with airway eosinophilia include, but are not limited to, eosinophilic asthma, eosinophilic COPD, eosinophilic bronchitis, and airway eosinophilia associated with viral infections, including, but not limited to, rhino virus. (Shinohara, et al. *Allergol Int.* 2008 Dec. 1; 57(4); Wos, et al. *Am J Respir Crit Care Med.* 2008; Handzel, et al. T cells. *J Immunol.* 1998 Feb. 1; 160(3):

1279-84.PMID; Mercer, et al. *Respir Res.* 2005; 6:151; and Saetta, et al. *Clin Exp Allerg* 1996; 26:766-774).

As used herein "refractory asthma" refers to a condition wherein a patient has one or both major criteria and two minor criteria as set forth below:

Table 1: Major Criteria and Minor Criteria for Refractory Asthma

Major Characteristics

In order to achieve control to a level of mild-moderate persistent asthma:
1. Treatment with continuous or near continuous (≥50% of year) oral corticosteroids
2. Requirement for treatment with high-dose inhaled corticosteroids:

| Drug | Dose (µg/d) | Dose (puffs/d) |
|---|---|---|
| a. Beclomethasone dipropionate | >1,260 | >40 puffs (42 µg/inhalation) |
|  |  | >20 puffs (84 µg/inhalation) |
| b. Budesonide | >1,200 | >6 puffs |
| c. Flunisolide | >2,000 | >8 puffs |
| d. Fluticasone propionate | >880 | >8 puffs (110 µg), >4 puffs (220 µg) |
| e. Triamcinolone acetonide | >2,000 | >20 puffs |

Minor Characteristics
1. Requirement for daily treatment with a controller medication in addition to inhaled corticosteroids, e.g., long-acting β-agonist, theophylline, or leukotriene antagonist
2. Asthma symptoms requiring short-acting β-agonist use on a daily or near daily basis
3. Persistent airway obstruction ($FEV_1$<80% predicted; diurnal PEF variability>20%)
4. One or more urgent care visits for asthma per year
5. Three or more oral steroid "bursts" per year
6. Prompt deterioration with ≤25% reduction in oral or inhaled corticosteroid dose
7. Near fatal asthma event in the past
   *Requires that other conditions have been excluded, exacerbating factors treated, and patient felt to be generally adherent.

Fahy, J. Am. J. Respir. Crit. Care Med., Volume 162, Number 6, December 2000, 2341-2351

As used herein "severe asthma" is meant to include patients with refractory asthma. Patients with severe asthma may not necessarily have airflow obstruction all of the time, and may or may not have airway hyperresponsiveness but may suddenly deteriorate on a background of relatively stable disease (on treatment). "Severe asthma" is also understood in the art to be defined by various clinical scales other than the ATS such as guidelines set for by *Global Strategy for Asthma Management and Prevention*, Global Initiative for Asthma (GINA) 2007 as well as other guidelines known in the art.

As used herein, "reduce" or "reducing" eosinophils refers to a decrease in the amount of eosinophils observed in the blood and/or sputum of a patient after administration at least one anti-IL-5 antibody.

As used herein "co-administration" or "co-administering" as used herein refers to administration of two or more compounds to the same patient. Co-administration of such compounds may be simultaneous or at about the same time (e.g., within the same hour) or it may be within several hours or days of one another. For example, a first compound may be administered once weekly while a second compound is co-administered daily.

As used herein "disorder associated with excess eosinophil production" means any disorder or disease in which atypical symptoms may manifest due to the production of eosinophils. Disorders associated with excess eosinophil production include but are not limited to, eosinophilic bronchitis, atopic asthma, atopic dermatitis, allergic rhinitis, non-allergic rhinitis, asthma, severe asthma, chronic eosinophilic pneumonia, allergic bronchopulmonary aspergillosis, coeliac disease, Churg-Strauss syndrome (periarteritis nodosa plus atopy), eosinophilic myalgia syndrome, hypereosinophilic syndrome, oedematous reactions including episodic angiodema, helminth infections, eosinophilia associated with parasite infection and/or the treatment of parasitic infection, onchocercal dermatitis and Eosinophil-Associated Gastrointestinal Disorders, including but not limited to, eosinophilic oesophagitis, eosinophilic gastritis, eosinophilic gastroenteritis, eosinophilic enteritis and eosinophilic colitis, nasal micropolyposis and polyposis, aspirin intolerance, asthma and obstructive sleep apnoea. Eosinophil-derived secretory products have also been associated with the promotion of angiogenesis and connective tissue formation in tumours and the fibrotic responses seen in conditions such as chronic asthma, Crohn's disease, scleroderma and endomyocardial fibrosis (Munitz A, Levi-Schaffer F. Allergy 2004; 59: 268-75, Adamko et al. Allergy 2005; 60: 13-22, Oldhoff, et al. Allergy 2005; 60: 693-6).

The therapeutic response induced by the methods of this invention is produced by the binding on an anti-IL-5 antibody to human IL-5 and thus subsequently blocking eosinophil stimulation. Thus, the methods of the present invention are highly desirable for those persons experiencing eosinophilic bronchitis.

Methods are provided herein for treating eosinophilic bronchitis, comprising administering to said human suffering from eosinophilic bronchitis a composition comprising at least one anti-IL-5 antibody. In some aspects, said human suffering from eosinophilic bronchitis has steroid-dependent eosinophilic bronchitis. In some aspects, the steroid is prednisone and/or prednisolone. The anti-IL antibody may be neutralizing. In another aspect, the at least one anti-IL-5 antibody is humanized. The least one anti-IL-5 antibody may comprise a heavy chain comprising SEQ ID NO: 19. The at least one anti-IL-5 antibody may comprise a light chain comprising SEQ ID NO: 21. In yet another aspect, the human is suffering from at least one additional disorder associated with excess eosinophil production selected from the group consisting of atopic asthma, atopic dermatitis, allergic rhinitis, non-allergic rhinitis, asthma, severe asthma, chronic eosinophilic pneumonia, allergic bronchopulmonary aspergillosis, coeliac disease, Churg-Strauss syndrome, eosinophilic myalgia syndrome, hypereosinophilic syndrome, oedematous reactions including episodic angiodema, helminth infections, eosinophilia associated with parasitic infection and/or the treatment of parasitic infection, onchocercal dermatitis eosinophilic oesophagitis, eosinophilic gastritis, eosinophilic gastroenteritis, eosinophilic enteritis, eosinophilic colitis, nasal micropolyposis, nasal polyposis, aspirin intolerance asthma, obstructive sleep apnoea, chronic asthma, Crohn's disease, scleroderma and endomyocardial fibrosis.

In yet another aspect, the composition comprising at least one anti-IL-5 antibody is administered intravenously. The composition comprising at least one anti-IL-5 antibody may be administered at a dose of 750 mg. The intravenous dose may be administered intravenously over 30 minutes. In another aspect, the composition comprising at least one anti-IL-5 antibody may be administered intravenously over a time range of about 10 minutes to about 4 hours or more specifically over a range of about 20 minutes to about 60 minutes. In another aspect of the present invention the composition comprising at least one anti-IL-5 antibody is administered subcutaneously, which may be at a dose of 250 mg. A subcutaneous dose may be administered one to three times or more to a human.

In yet another aspect, the human is receiving prednisone and/or prednisolone for said steroid-dependent eosinophilic bronchitis and said prednisone is reduced by at least about 90% in said human suffering from steroid-dependent eosinophilic bronchitis after treatment with said composition comprising at least one anti-IL-5 antibody. The human suffering from steroid-dependent eosinophilic bronchitis experiences a statistically significant reduction in exacerbations of eosinophilic bronchitis after receiving at least said composition comprising at least one anti-IL-5 antibody. The eosinophil level in said human are reduced to within normal limits, which is understood in the art and can be measured by a variety of methods including, but not limited to, bronchial scrubbing. By way of example, within normal limits would include, but would not be limited to, quantitative sputum cell counts having eosinophils less than 2%. The eosinophil levels remain within normal limits for at least 8 weeks after the last dose of said composition comprising anti-IL-5 antibody. Eosinophil levels may be reduced in blood and/or sputum.

In another aspect, methods are provided for treating a human with eosinophilic bronchitis wherein said composition comprising at least one anti-IL-5 antibody comprises a first anti-IL-5 antibody and a second anti-IL-5 antibody. The composition comprising at least one anti-IL-5 antibody may be co-administered with a steroid.

The present invention also provides methods for reducing eosinophils in a human in suffering from eosinophilic bronchitis, comprising administering a composition comprising a first anti-IL-5 antibody and a second anti-IL-5 antibody. Methods are also provided herein wherein at least one anti-IL-5 antibody is co-administered with a steroid.

The current invention also provides use of at least one anti-IL-5 antibody in the manufacture of a medicament for the treatment of eosinophilic bronchitis. The present invention provides use of an anti IL-5 antibody or fragment thereof for treatment of eosinophilic bronchitis comprising administering to a patient in need thereof a composition comprising at least one anti-IL-5 antibody. Also provided herein are pharmaceutical compositions capable of treating eosinophilic bronchitis or alleviating the symptoms produced thereby and formulated for the methods and uses described herein. The present invention provides an anti-IL-5 antibody for use in the treatment of eosinophilic bronchitis, for administration alone or in combination with a steroid. The anti-IL-5 antibodies of the present invention also provide anti-IL-antibodies for all of the methods and uses described herein.

EXAMPLES

The following examples illustrate various aspects of this invention. The results of Example 1 are published in Parameswaran, et al. *The New Engl J Med* 360(10):985-993 (2009), which is incorporated by reference herein in its entirety.

Example 1

The study was a randomized, placebo-controlled, parallel group trial of up to 26 weeks. Patients were seen every two weeks and were randomized to treatment at week 2. Humanized monoclonal antibody to IL-5, mepolizumab, was given at a dose of 750 mg or placebo over 30 minutes at weeks 2, 6, 10, 14, and 18. The dose of prednisone was reduced at weeks 6, 10, 14, 18, and 22, except in patients who had required prednisone in a daily dose of 10 mg or more. The variables measured every two weeks were: Juniper Asthma Control Questionnaire (ACQ), symptom Likert score, maximal expiratory flow-volume curves to measure $FEV_1$, and slow vital capacity (VC) before and 15 minutes after salbutamol 200 μg, sputum quantitative cell counts and blood eosinophils. As a result of prednisone reduction, the patients could have a clinical exacerbation or develop bothersome steroid withdrawal symptoms. Exacerbations were defined by an increase in salbutamol use of 4 or more puffs/day or of nocturnal or waking respiratory symptoms on two consecutive days, or by a fall in post-salbutamol $FEV_1 > 15\%$ from the randomization visit or by a 2-point change in the Likert score for cough or as decided by the investigator.

Spirometry was performed according to the American Thoracic Society recommendations (American Thoracic Society, Standardization of Spiromerty, 1994 update, *Am J Respir Crit Care Med,* 152:1107-1136 (1995)) and predicted values were obtained from Crapo, et al. (Crapo, et al. *Am Rev Respir Dis,* 123:659-94 (1981)). Asthma control was assessed using the validated Asthma Control Questionnaire (Juniper, et al, *Eur Respir J,* 14:902-7 (1999)). In addition, symptoms of cough, wheeze, chest tightness and shortness of breath were evaluated for the seven days prior to each visit on a 7-point Likert scale (7 no symptoms, 1 worse) (Guyatt, et al., *J Chronic Dis,* 40:1129-33 (1987)). Sputum was induced and processed as described by Pizzichini, et al. (Pizzichini, et al. *Eur Respir J,* 9:1174-1180 (1996)). Airway responsiveness to methacholine was measured using the tidal breathing method described by Cockcroft, et al. (Cockcroft, et al. *Clin Allergy,* 7:235-43 (1977)) after withholding β-agonists for 24 hours.

Exacerbations for this example were defined as either a patient-initiated increase in their daily dose of albuterol of four or more puffs to control symptoms of chest tightness or as any one of the following: nocturnal or waking respiratory symptoms on two consecutive days, a decrease of more than 15% in the $FEV_1$ from the label at randomization after the use of albuterol, or a 2-point worsening in the Likert score for cough by the investigators at their discretion on the basis of general clinical worsening. For the latter exacerbation, sputum-cell counts were not known to the treating physician at the time this decision was made and were not considered in the definition of exacerbations.

Exacerbations, unless accompanied by sputum neutrophilia, were treated with 30 mg of prednisone for 7 days. During this time, the patient was withdrawn from the study and was seen again at 2 and 4 weeks. If the exacerbation was accompanied by neutrophilic airway inflammation (total cell count, $>15 \times 10^6$ per gram of sputum; neutrophils, >80%), it was treated with 500 mg of amoxicillin-clavulanic acid twice daily for 10 days; patients with neutrophilic exacerbations were not withdrawn from the study, and they continued with the protocol for prednisone reduction.

The sample size was based on the primary outcome of the proportion of patients who would have exacerbations in each treatment arm. It was expected that all patients on the placebo would exacerbate when the dose was reduce by 50%, while not more that 4 patients on the active arm would exacerbate for a similar dose reduction. The study had 90% power to detect this difference. Between group comparisons of normally distributed data were compared using unpaired-t test and non-normal data were compared using Median test in an intention-to treat analysis. Proportional data was analyzed using Fisher's exact test. Cumulative probability and time to exacerbation between treatment groups were compared by Cox's proportional hazards methods. All tests were 2-sided and significance was accepted at 95% level and the analyses were done using the Statistical Package for Social Sciences, version 13.0 (SPSS, Chicago, Ill.).

Patients meeting the following inclusion criteria were enrolled in a study of anti-IL5 monoclonal antibody therapy for eosinophilic bronchitis sputum eosinophilia in patients with asthma chronically treated with systemic and high dose inhaled corticosteroids:

- Adult patients, aged 18-70 years, who have been followed as an outpatient and who have been found to require a minimum dose of prednisone treatment (in addition to high-dose inhaled steroid treatment) to prevent frequent exacerbations associated with induced sputum eosinophilia.
- Patients who, at screening and baseline visits, demonstrate sputum eosinophilia and symptoms. The symptoms may effect activity and sleep but should not, in the opinion of the treating physician, be severe enough to be of concern.
- While $FEV_1$ after withholding bronchodilators appropriately, before and after inhaled salbutamol (200 mg), and methacholine PC20 will be measured, these need not be abnormal since the prednisone is required for the control of eosinophilic bronchitis and any clinical consequences of this, and because the bronchitis can occur without these features of asthma.
- On the same doses of corticosteroids for a least one-month.

Figure 1:
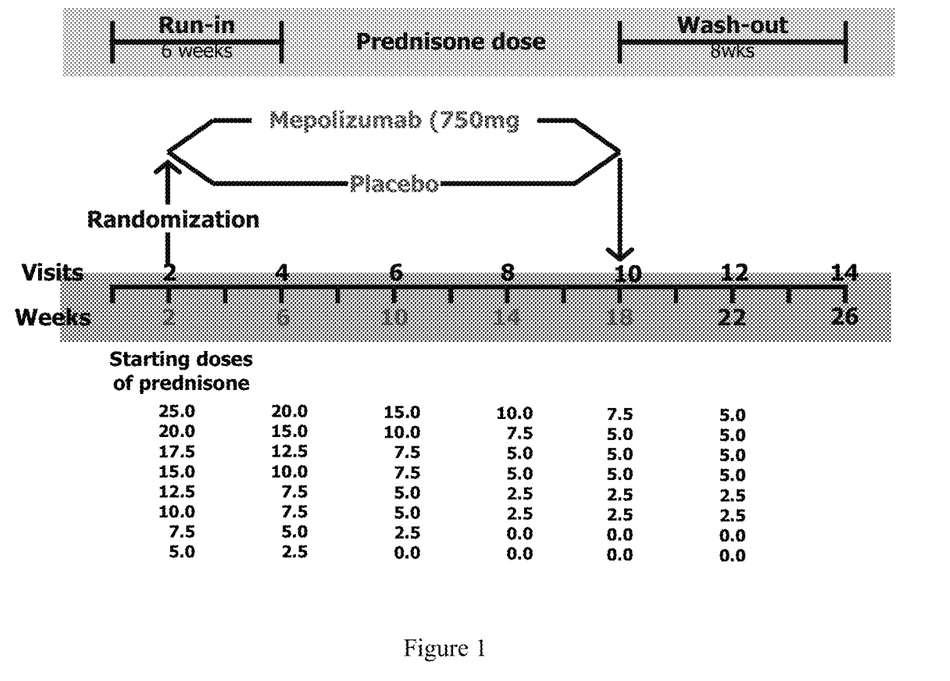
FIG. 1: Study Design as described in Example 1.

The study was divided into 3 sequential study periods as follows and presented in FIG. 1:

Period 1: Symptomatic eosinophilic bronchitis (with or without asthma) on the same dose of prednisone for 6-weeks or more.
Period 2: Standardized prednisone reduction (and inhaled steroid if prednisone is discontinued during the study treatment) at intervals of 4-weeks until there is a clinical and eosinophilic exacerbation or bothersome steroid withdrawal effects.
Period 3: Washout.

The patients were seen every 2 weeks. Intravenous injections of an anti-IL-5 antibody (mepolizumab) 750 mg or placebo were given at weeks 2, 6, 10, 14 and 18. Doses of prednisone were reduced in a standard way. A summary of patient demographics and baseline characteristics is presented in Table 2.

TABLE 2

Demographic and Clinical Characteristics of Patients at Baseline*

| Characteristics | Mepolizumab (n = 9) | Placebo (n = 11) |
|---|---|---|
| Age (years) | 56.4 ± 10.9 | 58.2 ± 7.1 |
| Gender, Male (no. of patients) | 4 | 8 |
| Height, cm | 166.2 ± 14.5 | 168.6 ± 9.9 |
| Weight, kg | 85.8 ± 16.7 | 89.5 ± 14.9 |
| Duration of symptoms, y | 13.3 ± 10.3 | 12.5 ± 9.59 |
| $FEV_1$ | | |
| Previous minimum† | | |
| Value (liters) | 1.4 ± 0.6 | 1.6 ± 0.5 |
| % of predicted value | 48 ± 17 | 52 ± 13 |
| Previous maximum† | | |
| Improvement with bronchodilator (%) | 28.4 ± 12.03 | 24.6 ± 10.6 |
| Decrease during exacerbation (%) | 42.0 ± 16.9 | 45.5 ± 13.7 |
| Current postbronchodilation | | |
| % of predicted value | 66.6 ± 18.3 | 74.3 ± 17.9 |
| Ratio of $FEV_1$ to vital capacity (%) | 63.8 ± 16.2 | 65.9 ± 13.1 |
| Sputum eosinophils | | |
| Median | 16.6 | 4.0 |
| Range | 1.6-54.3 | 0-35.3 |
| Duration of daily use of prednisone (years) | 9.3 ± 7.6 | 8.9 ± 8.5 |
| Prednisone (mg/day) | | |
| Median | 10 | 10 |
| Range | 5-25 | 2.5-20 |
| Inhaled Corticosteroids (µg/day) | | |
| Median | 1000 | 1000 |
| Range | 600-2000 | 1000-2000 |
| Short-acting β-agonist (no. of puffs/week) | 10 ± 6 | 9 ± 8 |
| Long-acting β-agonist (no. of patients) | 9 | 9 |
| Leukotriene-receptor antagonists (no. of patients) | 2 | 1 |
| Atopy (no. of patients) | 3 | 4 |
| Nasal polyp (no. of patients) | 3 | 5 |
| Smoking history of >10 pack years (no. of patients) | 2 | 3 |

*Plus-minus values are means ± SD. Values are those recorded at the time of screening unless otherwise stated. There were no significant differences between the two groups for any of the variables except the number of sputum eosinophils (P = 0.03).
$FEV_1$ denotes forced expiry volume in 1 second.
†Previous lowest and highest values for $FEV_1$ refer to the historic lowest and highest values recorded since the patients were first seen in the clinic.
‡The dose of inhaled corticosteroid is the equivalent of inhaled fluticasone.

Results

Nineteen of the 20 patients completed the study. One subject who received the active drug was withdrawn from the study after the 3rd infusion because of heart failure, but was included in the analysis. Thus, the main analyses included 20 patients, and the per-protocol analysis included only the 18 subjects who had airway eosinophilia at baseline.

Primary Outcomes

Exacerbations

Figure 2:
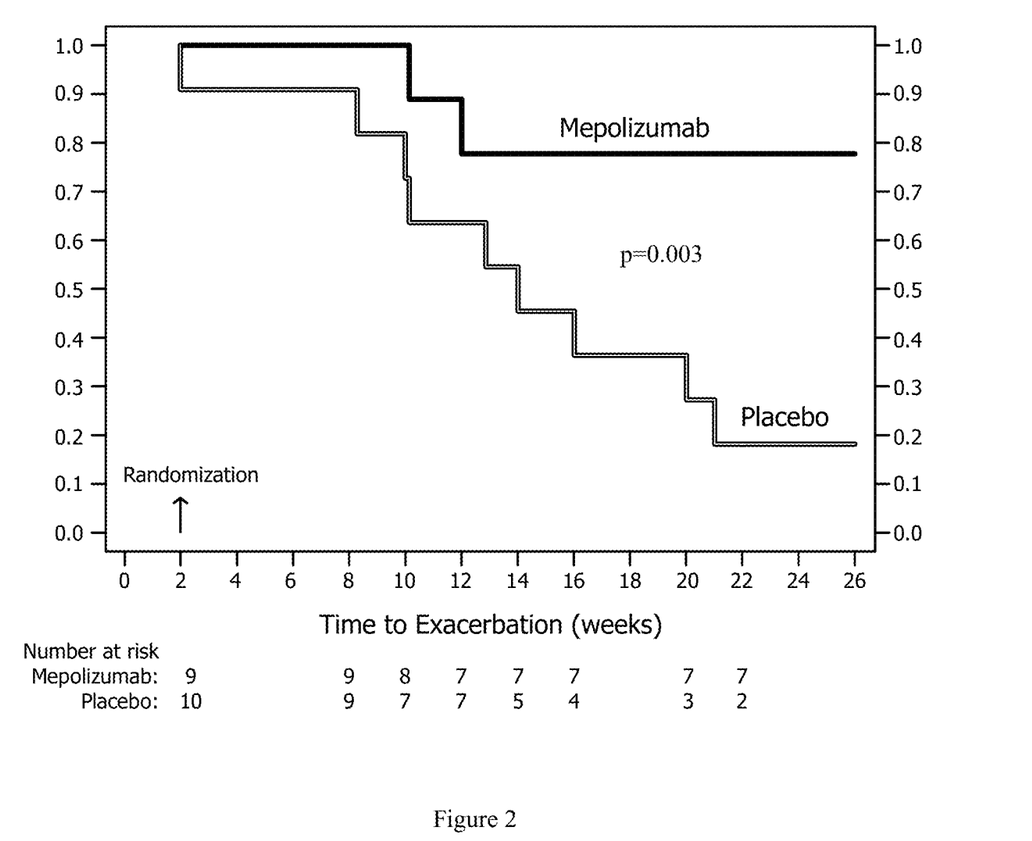
FIG. 2: Time until first exacerbation after randomization, as described in Example 1, section "Primary Outcomes" subsection "Exacerbations".

There were 12 asthma exacerbations in the placebo group. Nine were associated with sputum eosinophilia and three were associated with sputum neutrophilia, of which two were in a patient who was eventually treated for an exacerbation associated with sputum eosinophilia. Thus, 10 of the 11 patients in the placebo group had exacerbations that led to treatment with prednisone or antibiotics. In contrast, there were two events in the mepolizumab arm (1 neutrophilic exacerbation and one withdrawal due to adverse event) (p=0.008). Exacerbations were identified by a decline in $FEV_1$ and additional criteria in seven patients (one in the active treatment group and six in the placebo group), by an increase in $\beta_2$-agonist rescue (three patients in the placebo group), and by nocturnal symptoms (one patient in the placebo group). A change in the Likert scale alone or physician discretion was not used in any patient to identify an exacerbation or initiate a change in prednisone dose. The median time to exacerbation (irrespective of type of bronchitis) was 12 weeks in the placebo group and 20 weeks in the mepolizumab group (p=0.003). (FIG. 2).

There were also no exacerbations associated with neutrophilic bronchitis in the mepolizumab group while there were 3 in the placebo group.

Reduction in Prednisone Dose

In the mepolizumab group, patients had a mean (±SD) reduction of prednisone by 83.8%±33.4% of the maximum possible reduction per protocol compared to 47.4%±40.5% in the placebo group (p<0.04). In absolute terms, the mean dose of prednisone was reduced from 11.9 mg to 3.9 mg in the mepolizumab group and from 10.7 to 6.4 mg in the placebo group (median reduction in the two groups, from 10 to 5 mg) (P=0.11).

Pre-Specified Subgroup Analyses

Data for 8 of the 10 patients in the placebo group who had an exacerbation accompanied by sputum eosinophilia and were censored at that time, while none of the patients who received mepolizumab had an exacerbation associated with sputum eosinophilia (P=0.02). There were three exacerbations in the placebo group associated with sputum neutrophilia. In the mepolizumab group, there were five episodes of increased numbers of sputum neutrophils (in four patients) during routine visits, but the episodes were not associated with a change in the measures that defined an exacerbation and thus were not treated.

In the mepolizumab group, there was a mean (±SD) reduction in use of prednisone by 94.3%±12.9% of the maximum possible reduction per protocol compared with 47.5%±42.2% in the placebo group (p=0.01).

Pre-Specified Secondary Outcomes

Figure 3:
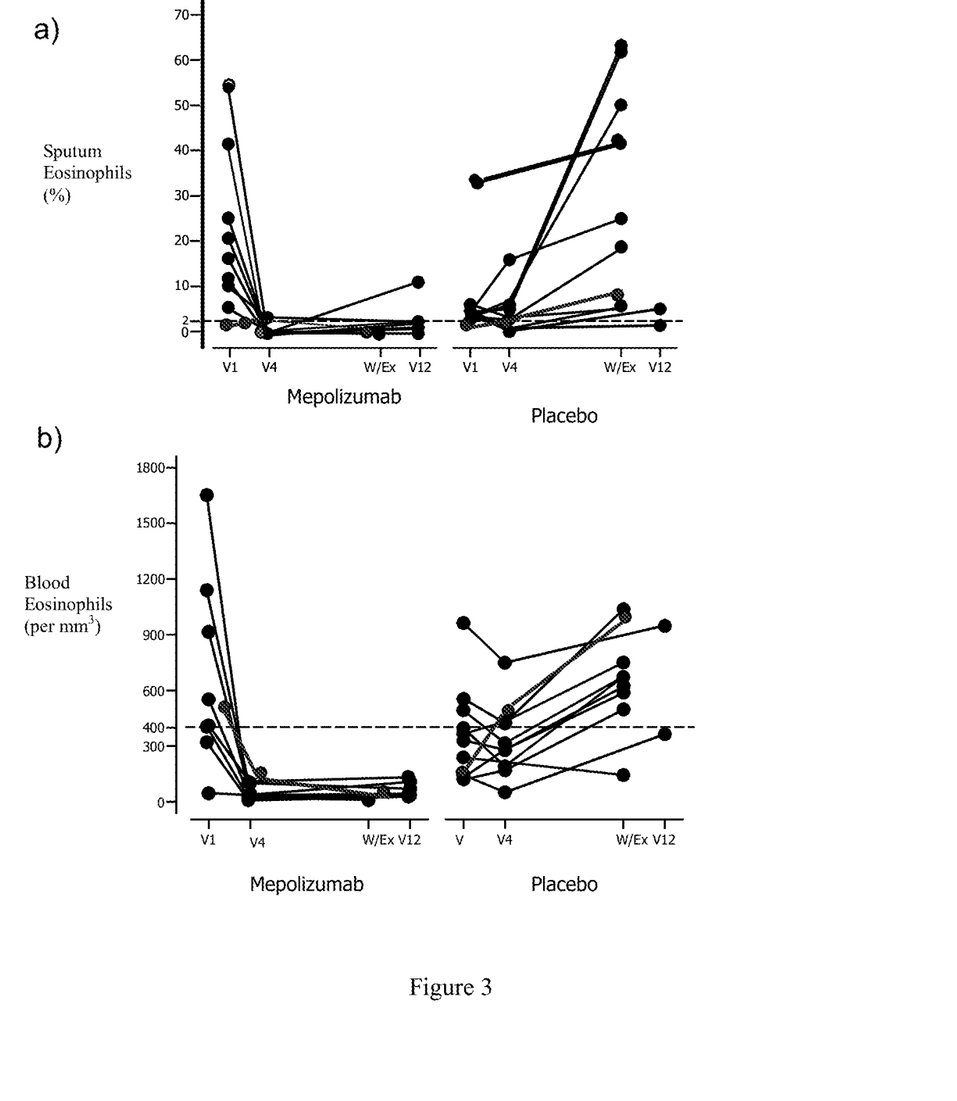

A single infusion of mepolizumab was associated with a reduction in the number of eosinophils to within normal limits in sputum (P=0.005) and blood (P=0.004). The levels remained within normal limits after reductions in the dose of prednisone for up to 8 weeks after the last infusion of mepolizumab (P=0.01). In contrast, a reduction in the dose of prednisone in the placebo group was associated with a significant increase in the number of eosinophils in sputum and blood (FIG. 3 and Table 3). There was no significant effect of mepolizumab on cell types other than eosinophils in sputum or blood, except for a significant reduction of lymphocytes in sputum 4 weeks after the fifth infusion (P=0.001). Mepolizumab treatment was associated with a modest improvement in $FEV_1$ (mean 300 ml), a nonsignificant improvement in asthma symptoms, and a significant improvement in scores on the Juniper Asthma Control Questionnaire (P=0.01) (Table 3 and FIG. 3).

Secondary Outcomes

A single infusion of mepolizumab reduced sputum and blood eosinophils to within normal limits, where they remained after reductions of prednisone dose (p<0.05) and for up to 8 weeks after the last infusion of mepolizumab. In contrast, sputum and blood eosinophils increased significantly with prednisone reduction in the placebo arm (Table 4). Mepolizumab treatment was associated with the improvement in $FEV_1$, asthma symptoms and asthma control questionnaire score as shown in Table 3.

A summary of variables before and after treatment for patients treated with mepolizumab are presented in Table 3. A summary of variables before and after treatment for patients treated with placebo are presented in Table 4.

TABLE 3

Variables before and after treatment with mepolizumab.

| Variables | Visit 1 Baseline | Visit 4 4 weeks post First dose | Visit 12 4 weeks post Last dose | Visit 14 8 weeks post Last dose |
|---|---|---|---|---|
| Number of patients | 9 | 9 | 7 | 7 |
| Sputum eosinophils (%) | | | | |
| Median | 16.6 | 0.0† | 1.3† | 0.3† |
| Range | 1.6-54.3 | 0-4.0 | 0.0-11.3 | 0.0-4.6 |
| Blood eosinophils ± per mm³ | 664.4 ± 492.5 | 49.5 ± 37.46† | 64.5 ± 37.94† | 76.3 ± 39.36† |
| $FEV_1$ after bronchodilation | | | | |
| Value ± Liters | 2.0 ± 0.88 | 2.1 ± 0.99 | 2.4 ± 1.06‡ | 2.3 ± 0.87 |
| % of predicted value | 66.6 ± 18.25 | 69.7 ± 17.7 | 71.9 ± 17.3‡ | 70.3 ± 13.2 |
| Juniper Asthma Control Questionnaire[a] | 1.9 ± 0.78 | 1.3 ± 0.91† | 1.2 ± 0.81† | 1.3 ± 0.91† |
| Cough Score[b] | 6.0 ± 0.82 | 5.2 ± 0.80† | 5.3 ± 0.96† | 5.5 ± 1.00 |
| Symptoms Score[c] | 29.4 ± 2.9 | 28.7 ± 4.9 | 31.6 ± 2.30 | 30.1 ± 4.02 |

Plus-minus values are means ± SD.

$FEV_1$ denotes forced expiry volume in 1 second.

†P < 0.05 for the comparison with baseline value.

‡P < 0.05 for the comparison with the corresponding change from baseline in the placebo group.

[a]The Juniper Asthma Control Questionnaire score ranges from 0 to 6, with higher scores indicating worse control.

[b]The cough score, which was measured only in patients without current asthma at screening, ranges from 1 to 7, with lower scores indicating a greater severity of symptoms.

[c]The symptoms score ranges from 7 to 35 with lower scores indicating greater severity of symptoms. This score consists of a composite rating of shortness of breath, chest tightness, wheezing, cough, and sputum production each graded on a 7-point Likert scale.

TABLE 4

Variables before and after treatment with placebo

| Variables | Visit 1 Baseline | Visit 4 4 weeks post First dose | Visit 12 4 weeks post Last dose | Visit 14 8 weeks post Last dose | Exacerbation | 4 weeks post Exacerbation |
|---|---|---|---|---|---|---|
| Number of patients | 11 | 10 | 2 | 2 | 9 | 9 |
| Sputum eosinophils (%) | | | | | | |
| Median | 4.0 | 3.0 | 3.2 | 5.0 | 25.3 | 4.0 |
| Range | 0-35.3 | 0.0-16.3 | 1.3-5.0 | 1.0-9.0 | 5.0-63.7 | 1.3-52.5 |
| Blood eosinophils ± per mm$^3$ | 352.1 ± 253.74 | 295.8 ± 207.39 | 657.0 ± 413.23 | 1224.0 ± 1383.03 | 655.5 ± 254.77 | 622.4 ± 498.4 |
| FEV$_1$ after bronchodilation | | | | | | |
| Value ± Liters | 2.2 ± 0.92 | 2.3 ± 0.94 | 2.3 ± 0.44 | 2.3 ± 0.39 | 2.0 ± 0.97 | 2.2 ± 0.8 |
| % of predicted value | 74.3 ± 17.8 | 75.6 ± 17.0 | 78.4 ± 20.9 | 78.1 ± 19.2 | 60.9 ± 20.7 | 74.4 ± 14.4 |
| Juniper Asthma Control Questionnaire$^a$ | 1.8 ± 0.92 | 1.6 ± 0.88 | 1.2 ± 0.52 | 1.2 ± 0.28 | 2.0 ± 1.04 | 1.6 ± 1.4 |
| Cough Score$^b$ | 6.3 ± 0.96 | 5.2 ± 1.2 | NA | NA | 5.8 ± 1.1 | 6.2 ± 1.0 |
| Symptoms Score$^c$ | 29.8 ± 5.14 | 30.8 ± 2.9 | 33.2 ± 1.56 | 32.5 ± 3.54 | 27.2 ± 4.18 | 29.4 ± 7.3 |

Plus-minus values are means ± SD.
FEV$_1$ denotes forced expiry volume in 1 second and NA not applicable.
$^a$The Juniper Asthma Control Questionnaire score ranges from 0 to 6, with higher scores indicating worse control.
$^b$The cough score, which was measured only in patients without current asthma at screening, ranges from 1 to 7, with lower scores indicating a greater severity of symptoms.
$^c$The symptoms score ranges from 7 to 35 with lower scores indicating greater severity of symptoms. This score consists of a composite rating of shortness of breath, chest tightness, wheezing, cough, and sputum production each graded on a 7-point Likert scale.

Safety

One patient in the mepolizumab group had progressive shortness of breath after receiving three infusions of the drug and was removed from the study. Investigators, who were unaware of study-group assignments, determined that this patient had preexisting coronary artery disease; the breathlessness was attributable to heart failure due to ischemic cardiomyopathy. The patient did not undergo endocardial biopsy or cardiac magnetic resonance imaging to rule out eosinophilic cardiomyopathy. One patient in the placebo group died suddenly at home, 6 months after the completing the full study. On autopsy, the cause of death was identified as sudden cardiac arrest possibly due to a ventricular tachyarrhythmia and was not ascribed to worsening asthma. One patient in the mepolizumab group reported having aches and tiredness when the prednisone dose was reduced to 2.5 mg. One patient in the placebo group had hypoadrenalism during the prednisone reduction from 12.5 mg to 5 mg per day (as demonstrated by a blunted cortisol response to a short corticotrophin stimulation test). There were no other serious adverse events. There were no significant abnormalities in blood chemical values attributable to mepolizumab.

Discussion

These data show that in the rare patient with asthma who continues to have sputum eosinophilia even when treated with oral prednisone and high dose inhaled corticosteroids, that treatment with a humanized monoclonal antibody against IL-5 allows a reduction in prednisone dose without the development of asthma exacerbations. These results are contrary to the negative results of earlier studies with a similar antibody (Leckie, et al. *Lancet* 2000; 356: 2144-8; Kips, et al. *Am J Respir Crit Care Med* 2003; 167: 1655-9; and Flood-Page, et al. *Am J Respir Crit Care Med* 2007; 176: 1062-71) in patients with more common forms of asthma and in concordance with those in hypereosinophilia syndrome (HES) (Klion, et al. *Blood* 2004; 103: 2939-2941; Garrett, et al. *J Allergy Clin Immunol* 2004; 113: 115-119; and Rothenberg, et al. *N Engl J Med* 2008; 358: 1215-28), and in two case report abstracts of asthma with sputum eosinophilia (Korn, et al. *Am J Respir Crit Care Med* 2007; 175: A486) and HES with asthma (Hargreave, et al. *Clin Exp Allergy* (abstract) 2004; 34: 1807).

In patients in the present study, with adult onset asthma, sputum eosinophilia that persisted in the presence of oral and inhaled corticosteroid treatment was reversed by the anti-IL-5 treatment and the patients improved clinically. In contrast, in the earlier studies, sputum eosinophils were either not measured, or there was little or no sputum eosinophilia at the onset of the study (Kips, et al. *Am J Respir Crit Care Med* 2003; 167: 1655-9 and Flood-Page, et al. *Am J Respir Crit Care Med* 2007; 176: 1062-71). None of the prior studies reported the effect of this treatment on the small subset of patients with baseline airway eosinophilia. It is thus possible that the lack of clinical benefit in previous trials was because the majority of patients randomized did not have the clinical phenotype we studied, persistent airway eosinophilia despite corticosteroid treatment.

This study has significant limitations. First, there was an imbalance in the starting percentage of sputum eosinophils between the two treatments, with the mepolizumab group having a higher sputum eosinophil count. It is possible that the patients who respond to mepolizumab are those with the highest numbers of eosinophils in sputum despite corticosteroid treatment. Second, although the study demonstrated a significant prednisone-sparing effect, there was no statistically significant difference in the more clinically meaningful outcome of the final prednisone doses in the two treatment groups. Third, the study relied on past objective evidence of asthma as indicated by variable airflow limitation. Since most patients had frequent exacerbations in the past and were on a maintenance dose of long-acting bronchodilator or had moderate airflow obstruction at baseline, the study did not re-test for albuterol reversibility or methacholine airway hyperresponsiveness in all patients at baseline. Fourth, the patients studied represent only a small proportion of patients with asthma and persistent sputum eosinophilia and our results likely do not apply to most patients with asthma. Fifth, despite efforts, investigators may not have remained completely blinded to treatment allocation because they were in part aware of sputum cell counts. Sixth the study is quite small and cannot be considered clinically directive.

In summary, intravenous mepolizumab reduces blood and sputum eosinophils and is prednisone-sparing in patients with asthma who had sputum eosinophils despite oral prednisone and high dose inhaled steroid treatment. This small pilot study is potentially clinically directive and highlights the importance of selecting subjects with airway eosinophilia to study an anti-eosinophil drug in asthma.

We claim:

1. A method for treating eosinophilic bronchitis, comprising:
   a) administering to a human suffering from said eosinophilic bronchitis a composition comprising at least one anti-IL-5 antibody, wherein said human was previously treated with a steroid; and
   b) reducing a dosage of said steroid for treating said human by at least 90% after treatment with said composition.

2. The method of claim 1, wherein said human has steroid dependent eosinophilic bronchitis.

3. The method of claim 2, wherein said steroid is prednisone or prednisolone.

4. The method of claim 2, wherein said human is receiving prednisone for said steroid dependent eosinophilic bronchitis and said prednisone is reduced by at least 90% in said human suffering from steroid dependent eosinophilic bronchitis after treatment with said composition.

5. The method of claim 2, wherein said human experiences a reduction in exacerbations of eosinophilic bronchitis after receiving at least one dose of said composition.

6. The method of claim 2, wherein said composition reduces an amount of steroid required by a patient to control exacerbations of eosinophilic bronchitis compared with placebo.

7. The method of claim 1, wherein said eosinophilic bronchitis is severe.

8. The method of claim 1, wherein said at least one anti-IL-5 antibody binds to human IL-5.

9. The method of claim 8, wherein said at least one anti-IL-5 antibody is neutralizing.

10. The method of claim 1, wherein said at least one anti-IL-5 antibody is humanized.

11. The method of claim 1, wherein said at least one anti-IL-5 antibody comprises a heavy chain comprising SEQ ID NO: 19.

12. The method of claim 1, wherein said at least one anti-IL-5 antibody comprises a light chain comprising SEQ ID NO: 21.

13. The method of claim 1, wherein said human is suffering from at least one additional disorder associated with excess eosinophil production selected from the group consisting of atopic asthma, atopic dermatitis, allergic rhinitis, non-allergic rhinitis, asthma, severe asthma, chronic eosinophilic pneumonia, allergic bronchopulmonary aspergillosis, coeliac disease, Churg-Strauss syndrome, eosinophilic myalgia syndrome, hypereosinophilic syndrome, oedematous reactions including episodic angiodema, helminth infections, eosinophilia associated with a parasitic infection, eosinophilia associated with treatment of parasitic infection, onchocercal dermatitis eosinophilic oesophagitis, eosinophilic gastritis, eosinophilic gastroenteritis, eosinophilic enteritis, eosinophilic colitis, nasal micropolyposis, nasal polyposis, aspirin intolerance asthma, obstructive sleep apnoea, chronic asthma, Crohn's disease, scleroderma and endomyocardial fibrosis.

14. The method of claim 1, wherein said composition is administered intravenously.

15. The method of claim 14, wherein said composition is administered at a dose of 750 mg.

16. The method of claim 14, wherein said composition is administered intravenously over 30 minutes.

17. The method of claim 1, wherein an eosinophil level in said human is reduced to within normal limits after at least one dose of said composition.

18. The method of claim 17, wherein said eosinophil level remains within normal limits for at least 8 weeks after a last dose of said composition.

19. The method of claim 17, wherein said eosinophil level in blood or sputum is reduced in said human.

20. The method of claim 1, wherein said composition comprises a first anti-IL-5 antibody and a second anti-IL-5 antibody.

21. The method of claim 1, wherein said composition is co-administered with a steroid.

22. The method of claim 1, wherein said human also suffers from asthma.

23. The method of claim 22, wherein said asthma is severe.

24. A method for treating eosinophilic bronchitis, comprising:
   a) administering to a human suffering from said eosinophilic bronchitis, a composition comprising at least one anti-IL-5 antibody, wherein said human was previously treated with a steroid, and wherein said human also suffers from asthma; and
   b) reducing a dosage of said steroid for treating said human by at least 90% after treatment with said composition.

* * * * *